US008467545B2

(12) United States Patent
Varma et al.

(10) Patent No.: US 8,467,545 B2
(45) Date of Patent: *Jun. 18, 2013

(54) NOISE REDUCTION SYSTEMS AND METHODS FOR VOICE APPLICATIONS

(75) Inventors: Ankur Varma, San Francisco, CA (US); Dinei A. Florencio, Redmond, WA (US)

(73) Assignee: Microsoft Corporation, Redmond, WA (US)

( * ) Notice: Subject to any disclaimer, the term of this patent is extended or adjusted under 35 U.S.C. 154(b) by 218 days.

This patent is subject to a terminal disclaimer.

(21) Appl. No.: 12/403,248

(22) Filed: Mar. 12, 2009

(65) Prior Publication Data

US 2009/0175462 A1 Jul. 9, 2009

Related U.S. Application Data

(63) Continuation of application No. 10/423,287, filed on Apr. 25, 2003, now Pat. No. 7,519,186.

(51) Int. Cl.

| | |
|---|---|
| ***H04B 15/00*** | (2006.01) |
| ***H04R 29/00*** | (2006.01) |
| ***H04R 3/00*** | (2006.01) |
| ***A61F 11/06*** | (2006.01) |
| ***G10K 11/16*** | (2006.01) |
| ***H03B 29/00*** | (2006.01) |
| ***H03G 3/20*** | (2006.01) |

(52) U.S. Cl.

USPC ........ 381/94.1; 381/56; 381/71.8; 381/71.12; 381/92; 381/94.2; 381/94.3; 381/94.7; 381/110

(58) Field of Classification Search

USPC ..................... 381/110, 94.1–94.3, 56–57, 92, 71.12–71.13, 94.7, 71.1–71.11; 704/275, 704/270, 272

See application file for complete search history.

(56) References Cited

U.S. PATENT DOCUMENTS

| | | | | |
|---|---|---|---|---|
| 4,305,131 | A | 12/1981 | Best | |
| 5,717,430 | A * | 2/1998 | Copland et al. | 345/168 |
| 5,974,382 | A * | 10/1999 | Fado et al. | 704/270 |
| 6,317,501 | B1 | 11/2001 | Matsuo | |
| 6,639,986 | B2 | 10/2003 | Kanamori et al. | |
| 6,748,086 | B1 * | 6/2004 | Venkatesh et al. | 381/71.4 |
| 7,519,186 | B2 | 4/2009 | Varma | |
| 2003/0063759 | A1 | 4/2003 | Brennan et al. | |

OTHER PUBLICATIONS

"Notice of Allowance", U.S. Appl. No. 10/423,287, (Jan. 9, 2009),8 pages.

Boll, Steven F., et al., "Suppression of Acoustic Noise in Speech Using Two Microphone Adaptive Noise Cancellation", 3 Pages, Dec. 1980.

Marcal, Luiz A., et al., "Noise Reduction in Speech Signals using a TMS320C31 Digital Signal Processor", 6 Pages, 2002.

(Continued)

*Primary Examiner* — Vivian Chin
*Assistant Examiner* — Douglas Suthers
(74) *Attorney, Agent, or Firm* — Wolfe-SBMC

(57) ABSTRACT

Various embodiments reduce noise within a particular environment, while isolating and capturing speech in a manner that allows operation within an otherwise noisy environment. In one embodiment, an array of one or more microphones is used to selectively eliminate noise emanating from known, generally fixed locations, and pass signals from a pre-specified region or regions with reduced distortion.

16 Claims, 13 Drawing Sheets

OTHER PUBLICATIONS

"Non Final Office Action", U.S. Appl. No. 10/423,287, (Jul. 31, 2006),22 Pages.

"Final Office Action", U.S. Appl. No. 10/423,287, (Oct. 19, 2006),22 Pages.

"Non Final Office Action", U.S. Appl. No. 10/423,287, (Apr. 9, 2007),32 Pages.

"Final Office Action", U.S. Appl. No. 10/423,287, (Sep. 20, 2007),36 Pages.

"Non Final Office Action", U.S. Appl. No. 10/423,287, (Jan. 9, 2008),37 Pages.

"Final Office Action", U.S. Appl. No. 10/423,287, (Jul. 22, 2008),41 Pages.

* cited by examiner

NOISE REDUCTION SYSTEMS AND METHODS FOR VOICE APPLICATIONS

PRIORITY

This application is a continuation of and claims priority under 35 U.S.C. §120 to U.S. application Ser. No. 10/423,287 filed Apr. 25, 2003, the disclosure of which is incorporated by reference herein in its entirety.

BACKGROUND

Typical computer-implemented voice applications in which a voice is captured by a computing device, and then processed in some manner, such as for voice communication, speech recognition, voice fingerprinting, and the like, require high signal fidelity. This usually limits the scenarios and environments in which such applications can be enabled. For example, environmental and other noise can degrade a signal associated with the desired voice that is captured so that the recipient of the signal has a difficult time understanding the speaker.

Many computer-implemented voice applications are often best employed in a context in which there is an absence of meaningful background or undesired speech. This necessarily limits the environments in which these voice applications can be used. It would be desirable to provide methods and systems that do not meaningfully inhibit the environments in which computer-implemented voice applications are employed.

SUMMARY

Various embodiments are directed to methods and systems that reduce noise within a particular environment, while isolating and capturing speech in a manner that allows operation within an otherwise noisy environment.

In accordance with one embodiment, an array of one or more microphones is used to selectively eliminate noise emanating from known, generally fixed locations, and pass signals from a pre-specified region or regions with reduced distortion. The array of microphones can be employed in various environments and contexts which include, without limitation, on keyboards, game controllers, laptop computers, and other computing devices that are typically utilized for, or can be utilized to acquire speech using a voice application. In such environments or contexts, there are often known sources of noise whose locations are generally fixed relative to the position of the microphone array. These sources of noise can include key or button clicking as in the case of a keyboard or game controller, motor rumbling as in the case of a computer, background speakers and the like—all of which can corrupt the speech that is desired to be captured or acquired.

In accordance with various embodiments, the sources of noise are known a priori and hence, the microphone array is used to capture one or more signals or audio streams. Once the signals are captured, the correlation across signals is measured and used to train an algorithm and build filters that selectively eliminate noise that exhibits such a correlation across the microphone array.

Additionally, one or more regions can be defined from which desirable speech is to emanate. The locations of the desirable speech are known a priori and hence, the microphone array is used to capture one or more audio signals associated with the desired speech. Once the signals are captured, the correlation across the speech signals is measured and used to train the algorithm and build filters that selectively pass the speech signals with reduced distortion.

Combining the noise reduction and speech capturing features provides a robust system that selectively attenuates noises such as key and button clicks, while amplifying speech signals emanating from the defined region(s).

DETAILED DESCRIPTION

Overview

The various embodiments described below are directed to methods and systems that reduce noise within a particular environment, while isolating and capturing speech in a manner that allows operation within an otherwise noisy environment.

In accordance with one embodiment, an array of one or more microphones is used to selectively eliminate noise emanating from known, generally fixed locations and/or sources, and pass signals from a pre-specified region or regions with reduced distortion. The array of microphones can be employed in various environments and contexts among which include, without limitation, on keyboards, game controllers, laptop computers, and other computing devices that are typically utilized for, or can be utilized to acquire speech using a voice application. In such environments or contexts, there are often known sources of noise whose locations are generally fixed relative to the position of the microphone array. These sources of noise can include key or button clicking as in the case of a keyboard or game controller, motor rumbling as in the case of a computer, background speakers and the like—all of which can corrupt the speech that is desired to be captured or acquired.

In accordance with various embodiments, the sources of noise are known a priori and hence, the microphone array is used to capture one or more signals or audio streams. Once the signals are captured, the correlation across signals is measured and used to train an algorithm and build or otherwise equip a device with a filter system that selectively eliminates noise that exhibits such a correlation across the microphone array.

Additionally, one or more regions or locations can be defined from which desirable speech is to emanate. The locations of the desirable speech are known a priori and hence, the microphone array is used to capture one or more audio signals associated with the desired speech. Once the signals are captured, the correlation across the speech signals is measured and used to train the algorithm and build filters that selectively pass the speech signals with reduced distortion.

Combining the noise reduction and speech capturing features provides a robust system that selectively attenuates noises such as key and button clicks, while amplifying speech signals emanating from the defined region(s).

In one particularly useful context, the methods and systems are employed in connection with a game controller. It is to be appreciated and understood that this context serves as an example only, and is not intended to limit application of the claimed subject matter, except where so specifically indicated in the claims.

The Game Controller Context

Figure 1:
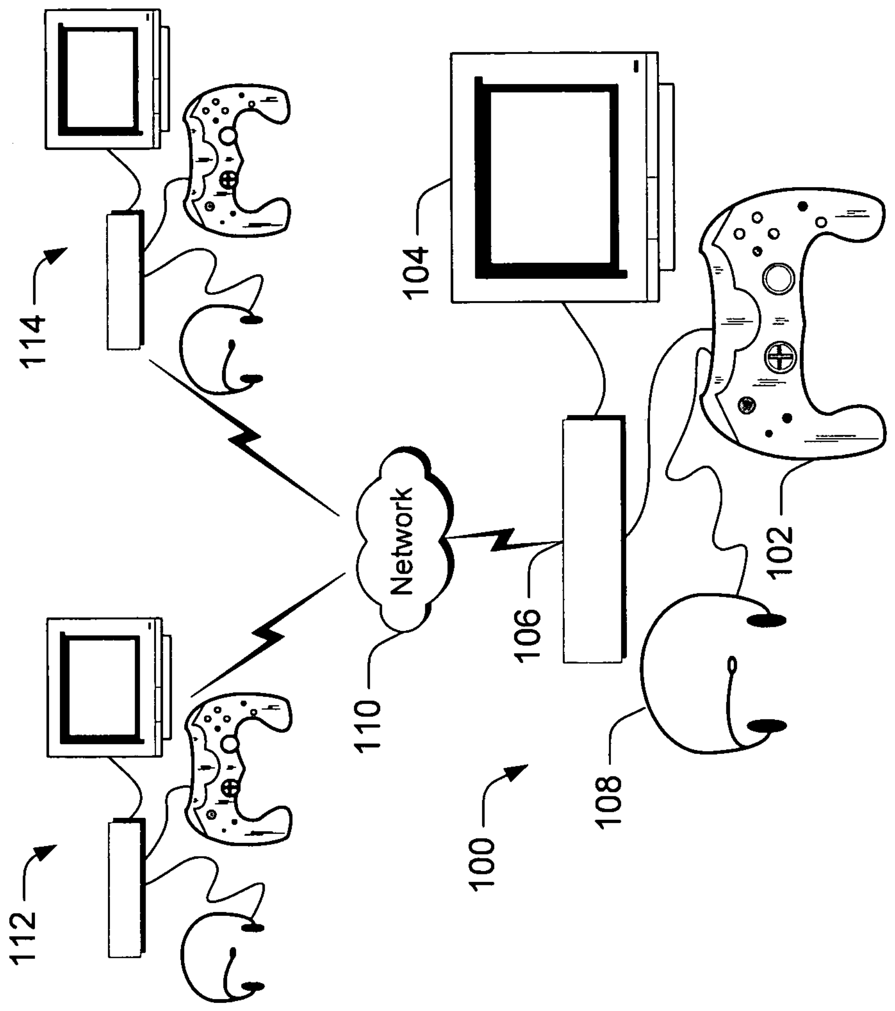
FIG. 1 illustrates a gaming environment in which various inventive methods and systems can be employed.

Before discussing the various aspects of the inventive embodiments, consider the game controller context, an example of which is illustrated in FIG. 1 generally at 100.

There, a game controller 102 is shown connected to a display 104 such as a television, and a game console 106. A headset 108 is provided and is connected to the controller 102 and includes one or more ear pieces and a microphone. One typical controller is an Xbox® Controller offered by the assignee of this document. One variety of this controller comes equipped with a number of analog buttons, analog pressure-point triggers, vibration feedback motors, an eight-way directional pad, menu navigation buttons, and the like—all of which can serve as noise sources.

In many typical gaming scenarios, a player using controller 102 engages in a game with other players using other controllers and game consoles. These other players can be dispersed across a network. For example, a network 110 allows players on other game systems 112, 114 to play against the player using controller 102. In order to communicate with one another, the players typically wear headsets, such as the one shown at 108.

Headsets have been found by some players to be too restrictive and can interfere with a player's movement during the game. For example, when a player plays a particular game, they may move around throughout the game. Having a cord that extends between the headset and the controller can, in some instances, unnecessarily tether the player to the console or otherwise restrict their movement.

Another issue associated with the use of a headset pertains to the inability of the headset to adequately reduce undesired noise that is generated during play of the game. As an example, consider the following. When the headset is in place on the player's head, the headset's microphone is fairly close to the player's mouth. The hope is that the microphone will pick up what the player is saying, and will attenuate undesired noise such as that produced by button clicking, other speakers who may be in the room, and the noise of the game itself. The problem here however, and one which people have complained about, is that when a game is being played, the game sound is really quite loud and is often picked up by the microphone on the headset. Thus, even though a player's mouth is physically near the headset's microphone, the loud game sounds often creep into the signal that is picked up by the microphone and transmitted to the other players. Needless to say, this makes for a poorer quality of sound and can degrade the game experience.

Thus, this scenario presents an interesting challenge to those who design games. In order to provide more freedom of movement for the player, it is desirable to find a way to remove the headset, or at least reduce its effect as far as a player's freedom of movement is concerned. Yet, it is also desirable to allow the players to effectively and conveniently communicate with one another. This interesting challenge has led to the various embodiments which will now be discussed below.

Sources of Noise and Speech

In accordance with several of the embodiments described herein, the methods and systems make use of the fact that the sources of noise and speech (whether desired speech that is to be transmitted, or undesired speech that is to be filtered) are generally known beforehand or a priori. These sources of noise and speech typically have fixed locations and/or sources and, in many cases, profiles that are readily identifiable.

Figure 2:
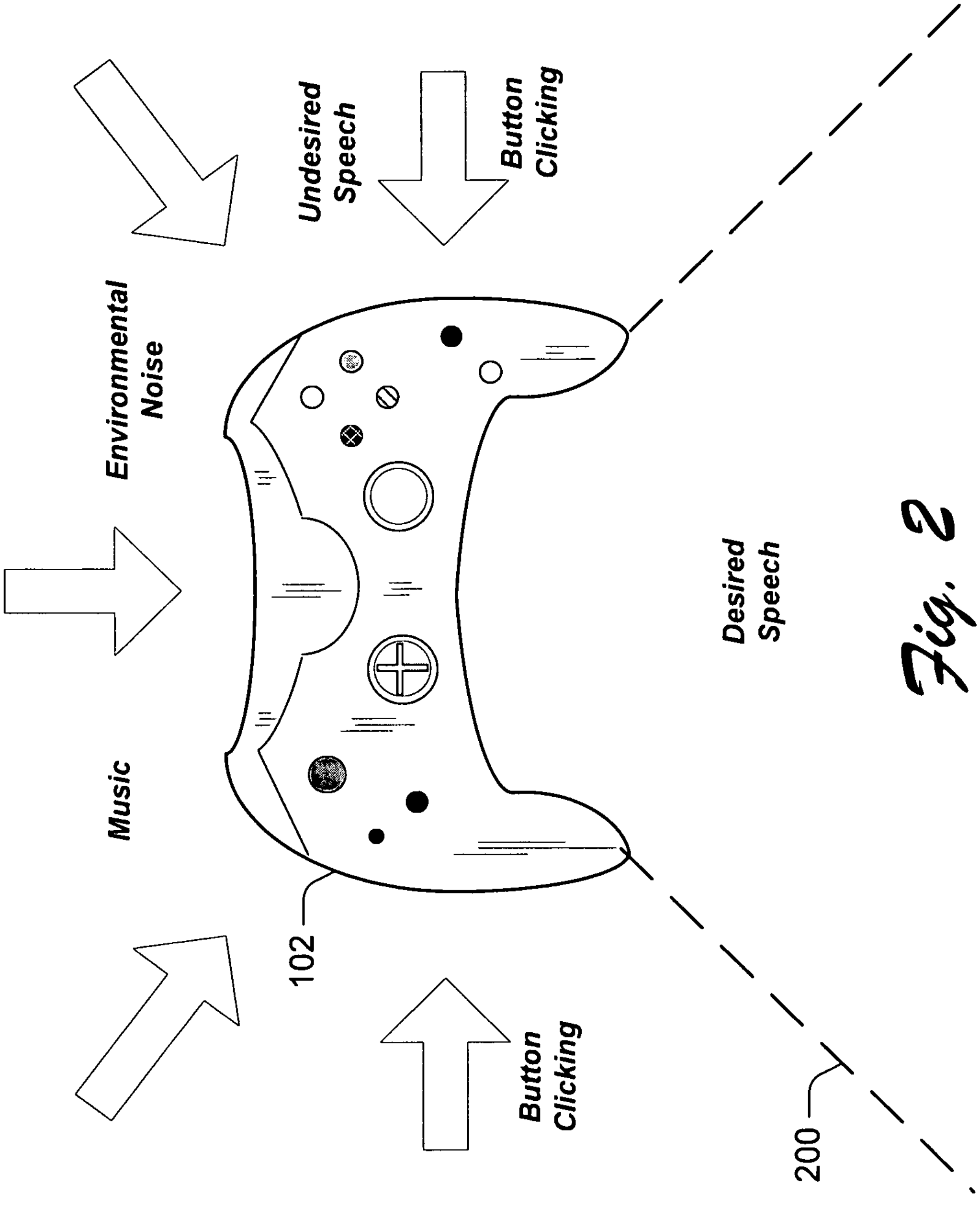
FIG. 2 illustrates an exemplary game controller.

As an example, consider FIG. 2 which is an enlarged illustration of the FIG. 1 game controller 102. Notice here that there are several sources of noise. Such noise can include environmental noise such as music, kids playing, noise from the room in which the console is located (which can include the game noise), and the like. This noise also includes the noise that is made by user-engagable input 8 mechanisms, such as the buttons, when the buttons are depressed by the player 9 during the course of the game. Such noise can also include such things as so-called undesired speech. Undesired speech, in the context of this example, comprises speech that emanates from an individual other than the individual playing the game on console 102. It is desirable to minimize, to the extent possible, this type of noise from the signal that is transmitted to the other players.

Notice also that there is a defined region 200 which is illustrated by the dashed line and within which desired speech typically occurs. In the context of this example, desired speech comprises speech that emanates from a player who is using the game controller to play the game. Throughout play of the game, and largely due to the fact that the game player must hold the game controller in order to play the game, the player's speech will typically emanate from within region 200.

Thus, the sources and locations of noise are typically known in advance with a reasonable degree of certainty. Likewise, the location within which desired speech occurs is typically known in advance with a reasonable degree of certainty. These locations tend to be generally fixed in position relative to the game controller. By knowing the sources and locations from which noise emanates, and the locations from which desired speech emanates, the inventive methods and systems can be trained, in advance, to recognize noise and desired speech, and can then take steps to filter out the noise signals while passing the desired speech signals for transmission.

One specific example of how this can be done is given below in the section entitled "Implementation Example."

Exemplary Game Controller

Figure 3:
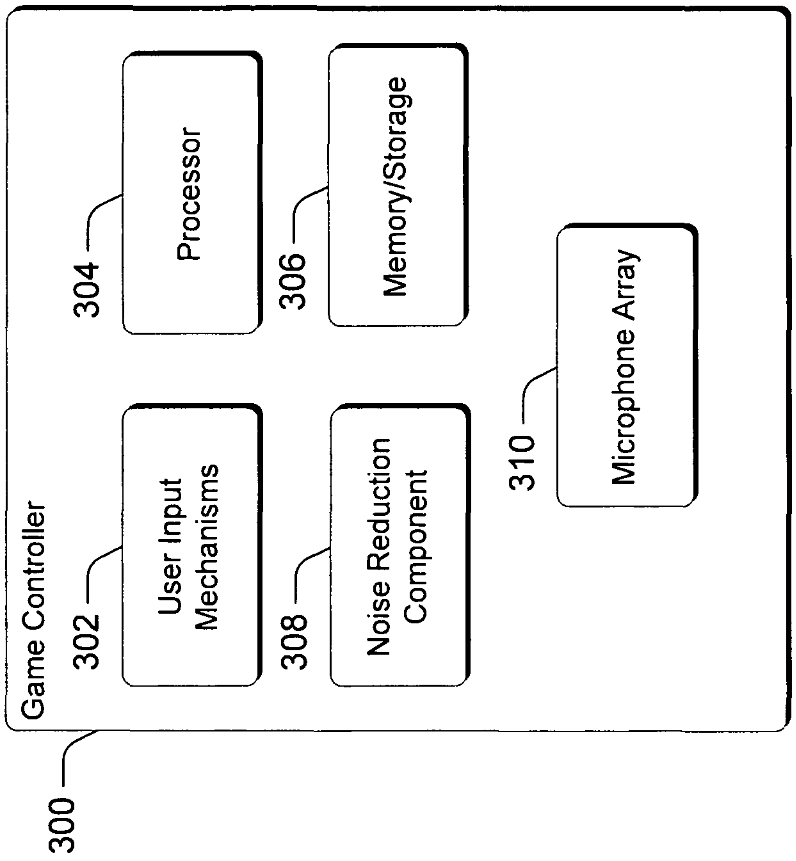
FIG. 3 illustrates an exemplary game controller and selected components in accordance with one embodiment.

FIG. 3 illustrates exemplary components of a system in the form of a game controller generally at 300, in accordance with one embodiment. While the described system takes the form of a game controller, it is to be appreciated that the various components described below can be incorporated into systems that are not game controllers. Examples of such systems have been given above.

Games controller 300 comprises a housing that supports one or more user input mechanisms 302 which can include buttons, levers, shifters and the like. Controller 300 also comprises a processor 304, computer-readable media such as memory or storage 306, a noise reduction component 308 and a microphone array 310 comprising one or more microphones. The microphone array may or may not include one or more headset-mounted microphones. In some embodiments, the noise reduction component can comprise software that is embodied on the computer-readable media and executable by the processor to function as described below. In other embodiments, various elements (e.g., processor 304, memory/storage 306, and/or noise reduction component 308) can be located in places other than the controller (e.g., in the console 106). In yet other embodiments, the noise reduction component can comprise a firmware component, or combinations of hardware, software and firmware.

It is to be appreciated and understood that the architecture of the illustrated game controller is not intended to limit application of the claimed subject matter. Accordingly, game controllers can have other architectures which, while different, are still within the spirit and scope of the claimed subject matter.

In the discussion that follows, operational aspects of the noise reduction component 308 and the microphone array 310 will be discussed as such pertains to the inventive embodiments.

Exemplary Method Overview

In accordance with one described embodiment, there are two separate but related aspects of the inventive methods and systems—a training aspect in which the noise reduction component is built and trained to recognize noise and desired speech, and an operational aspect in which a properly trained noise reduction component is set in use in the environment in which it is intended to operate. Each of these separate aspects is discussed below in a separately entitled section.

Training

Figure 4:
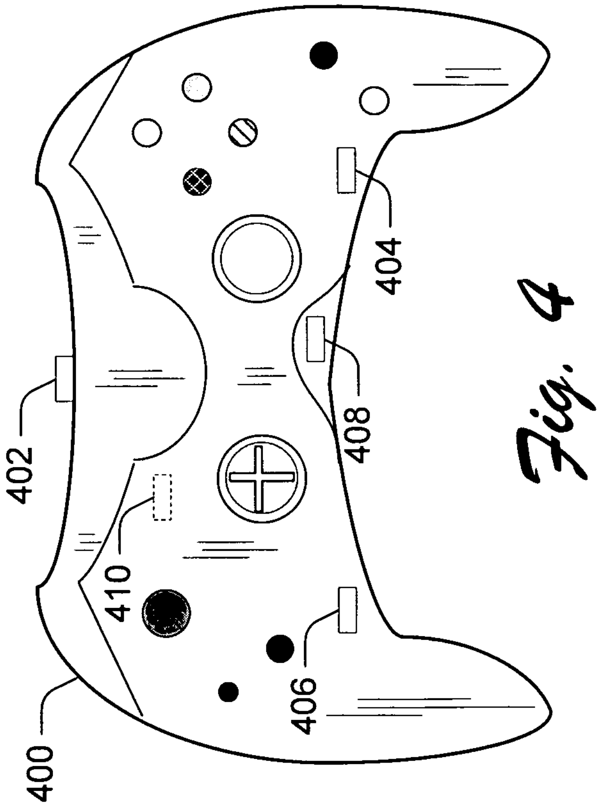
FIG. 4 illustrates an exemplary game controller and a microphone array in accordance with one embodiment.

FIG. 4 illustrates an exemplary game controller generally at 400 in accordance with one embodiment. Controller 400 comprises a microphone array which, in this example comprises multiple microphones 402-410. In this example, microphone 402 is mounted on the backside of the game controller away from the player; microphones 404, 406 are mounted on the housing of the upper surface of the game controller; microphone 408 is mounted inside or within the housing of the controller, as indicated by the portion of the housing which is broken away to show the interior of the housing; and microphone 410 is mounted on the underside of the controller.

The microphone array is used to acquire multiple different signals associated with sound that is produced in the environment of the game controller. That is, each individual microphone acquires a somewhat different signal associated with sound that is produced in the game controller's environment. This difference is due to the fact that the spatial location of each microphone is different from the other microphones.

During the training aspect, sounds constituting only noise and only desired speech can be produced separately for the microphones to capture. For example, in the noise-capturing phase, an individual trainer might physically manipulate the game controller's buttons or other user input mechanisms (without speaking) to allow each of the different microphones of the array to separately capture an associated noise signal. During the desired speech-capturing phase, the individual trainer might not manipulate any of the controller's buttons or user input mechanisms, but rather might simply position him or herself within the region where desired speech is normally produced, and speak so that the microphones of the array pick up the speech. During the noise-capturing and desired speech-capturing phases, each of the microphones acquires a somewhat different signal. For example, in the noise-capturing phase consider that a person stands in front of the game controller and speaks. Microphone 402 at the top of the controller will pick up a different signal than the signal picked up by microphone 408 inside of the controller. Yet, each signal is associated with the speech that emanates from the person in front of the game controller.

Similarly, in the desired speech-capturing phase, consider that a person emulating a player holds the game controller in the proper position and begins to speak. Microphones 404, 406 will pick up signals associated with the speech which are very different from the signal picked up by microphone 408 inside the controller's housing.

During the training aspect, these different signals, both noise and desired speech, are processed and, in accordance with one embodiment, cross correlated or correlated with one another to develop respective profiles of noise and desired speech. Cross correlation and correlation of signals is a process that will be understood by the skilled artisan. In the context of this document, the terms "cross-correlation" and "correlation" as such pertain to the matrices described below, are used interchangibly. One example of a specific implementation that draws upon the principles of cross correlation and correlation is described below in the section entitled "Implementation Example."

With an understanding of these noise and desired speech profiles, a filter system is constructed as a function of the cross correlated or correlated signals. The filter system can then be incorporated into a noise reduction component, such as component 308 (FIG. 3).

Once the filter system is constructed and incorporated into the game controller, the training aspect is effectively accomplished and the game controller can be configured for use in its intended environment.

Figure 5:
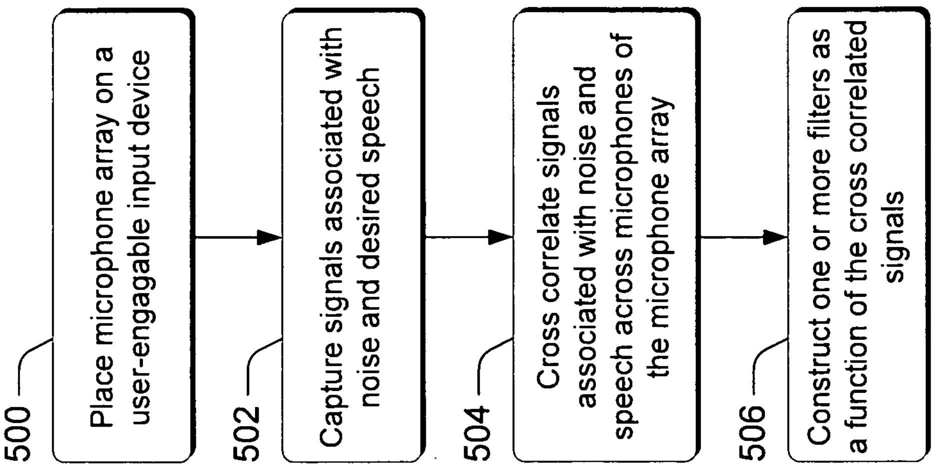
FIG. 5 is a flow diagram that describes steps in a method in accordance with one embodiment.

FIG. 5 is a flow diagram that describes steps in a training method in accordance with one embodiment. In the illustrated and described embodiment, the steps can be implemented in connection with a game controller such as the one shown and described in connection with FIG. 4.

Step 500 places a microphone array on a user-engagable input device. In one embodiment, the user-engagable input device comprises a game controller such as the one discussed above. Step 502 captures signals associated with noise and desired speech. This steps can be implemented by separately producing sounds associated with noise and desired speech. Step 504 cross correlates the signals associated with noise and correlates the signals associated with speech across the microphones of the microphone array. Doing so constitutes one way of building profiles of the noise and desired speech. Step 506 then constructs one or more filters as a function of the cross correlated and correlated signals.

In one embodiment, the filters are implemented in software and are hard coded into the game controller. For example, the filters can reside in the memory or storage component 306 (FIG. 3) and can be used by the controller's processor in the operational aspect which is described just below.

In Operation

Having constructed the filter system as described above, the filter system can be incorporated into suitable user-engagable input devices so that the devices are now configured to be employed in their noise-reducing capacity.

Figure 6:
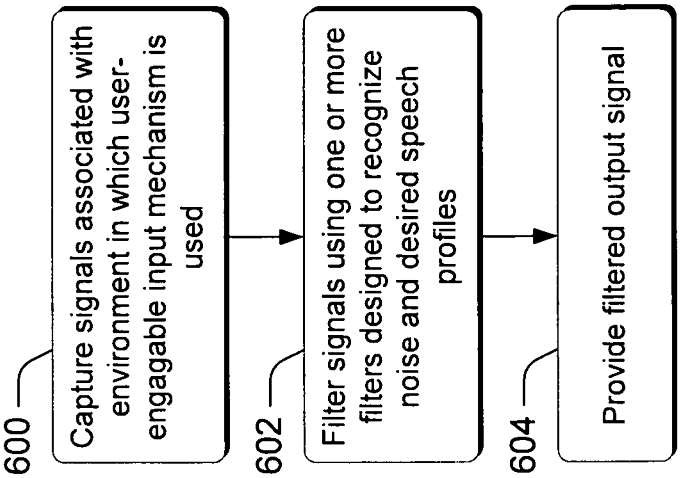
FIG. 6 is a flow diagram that describes steps in a method in accordance with one embodiment.

Accordingly, FIG. 6 is a flow diagram that describes steps in a noise-reduction method in accordance with one embodiment. The method can be implemented in connection with any suitable user-engagable input device such as the exemplary game controller described above.

Step 600 captures signals associated with an environment in which the user-engagable input device is used. Where the user-engagable input device comprises a game controller, this step can be implemented by capturing signals associated with the game-playing environment. These signals can constitute noise signals, desired speech signals and/or both noise and desired speech signals intermingled with one another. For example, as a game player excitedly uses the game controller to play a game with their friends on-line, the game player may rapidly press the controller's buttons while, at the same time, talk with the other on-line players. In this case, the signals that are captured would constitute both noise components and desired speech components. This step can be implemented using a microphone array such as array 310 in FIG. 3.

Step 602 filters the captured signals using one or more filters that are designed to recognize noise and desired speech signal profiles. As noted above, the profiles of the noise and desired speech signals can be constructed through a cross correlation and correlation process, an example of which is explored in more detail below. Filtering the captured signals enables the noise component of the signal to be reduced or attenuated so that the desired speech component is not lost or muddled in the signal. Step 604 provides a filtered output comprising an attenuated noise component and a desired speech component. This filtered output can be further processed and/or transmitted to the other players playing the game. Once example of further processing the filtered output signal is provided below in the section entitled "Threshold Processing of the Filtered Output Signal."

IMPLEMENTATION EXAMPLE

In the following implementation example, certain principles disclosed in pending U.S. patent application Ser. No. 10/138,005, entitled "Microphone Array Signal Enhancement", filed on May 2, 2002, and assigned to the assignee of this document, are used. This patent application is fully incorporated by reference herein.

Preliminarily, before describing the implementation example, consider the following. In above-referenced patent application, certain embodiments are directed to solving problems associated with so-called ambiguous noise—that is, noise whose origin and type are not necessarily fixed. To this end, these embodiments can be said to provide a dynamic solution that is adaptable to the particular environment in which the solution is employed. In the present case, to a large extent, the noise and indeed the desired speech with which the described solutions are employed is not ambiguous. Rather, most if not all of the noise and desired speech sources and locations are typically known in advance. Thus, the solution about to be described is given in the context of this non-ambiguous noise and desired speech.

It is to be appreciated, however, that the principles described in the referenced patent application can well be used to provide for dynamic, adaptable filtering solutions that can be used on the fly.

Calculating the Filters of the Filter System

In accordance with one embodiment, a number of spatial filters are computed as generalized Wiener filters having the form:

$$w_{opt}=(R_{ss}+\beta R_{nn})^{-1}(E\{ds\}),$$

where $R_{ss}$ is the correlation matrix for the desired signal (the desired speech signal), $R_{nn}$ is the correlation matrix for the noise component, $\beta$ is a weighting parameter for the noise component, and E{ds} is the expected value of the product of the desired signal d and the actual signal s that is received by a microphone.

In the described embodiment, the source and nature of the noise components (such as button clicking and the like) is known. Additionally, the desired speech component is known. Thus, there is full knowledge a priori of the noise and speech components. With this full knowledge of the noise and desired speech, the filter system can be constructed and trained. The building of the filter system coincides with the training aspect described above in the section entitled "Training."

Figure 7:
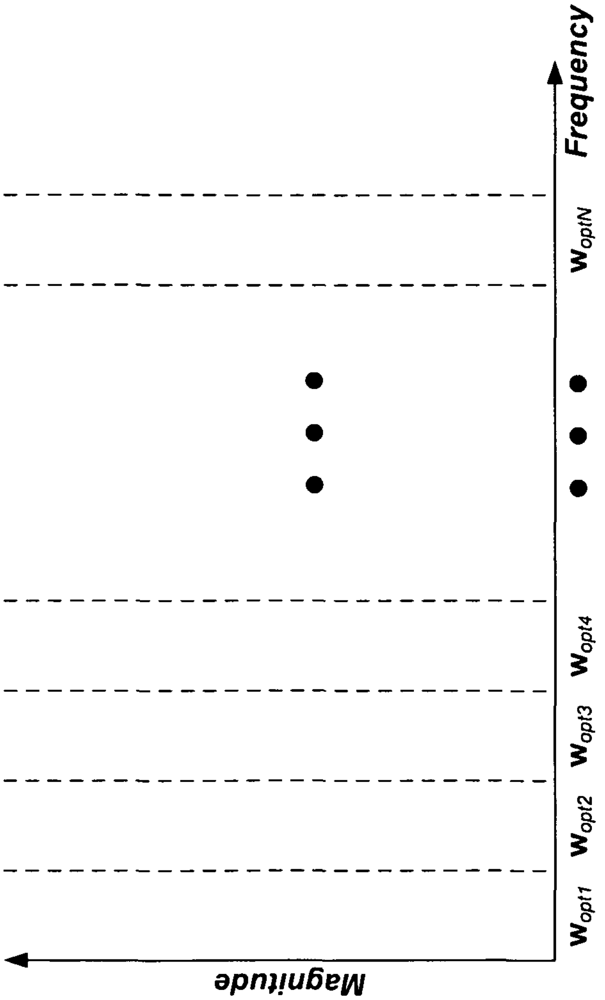
FIG. 7 is an illustration of a number of frequency bins and associated spatial filters in accordance with one embodiment.

In accordance with one embodiment, the frequency range over which signal samples can occur is divided up into a number of non-overlapping bins, and each bin has its own associated filter. For example, FIG. 7 shows a number of frequency bins with their associated filter. In a preferred embodiment, 64 frequency bins and hence, 64 individual filters are utilized. As will be appreciated by the skilled artisan, in this embodiment, the number of bins over which the frequency range is divided drives the number of filters that are employed. The larger the number of bins (and hence filters), the better the filtered output will be, but at a higher performance cost. Thus, in the present example, having 64 bins constitutes a good compromise between performance and cost.

Another relevant point is that the filter may have more than one tap per frequency per channel. In such case, the correlation matrices will include several (delayed) samples of the same signal.

As an example, in a situation where we have three microphones and we use 64 frequency bins, and one tap per bin, we will have a total of 64 filters. Each filter will have a total of three taps (one per microphone), and if the transform is complex, each filter coefficient is a complex number. Each of the correlation matrices used in computing the filters will be a 3×3 matrix. For example, for the frequency bin n, $R_{ssn}$(ij) can be computed as:

$$Rssn(i,j)=E\{Xi(n)\cdot Xj^*(n)\},$$

Where Xi(n) is the n-th coefficient of the transform of the signal at microphone I, and * denotes complex conjugate. The case of several taps per channel can be treated as if the past frame was an extra microphone.

Once the filter system has been built and trained, it can be incorporated into a suitable device, such as a game controller, in the form of a noise reduction component.

Figure 8:
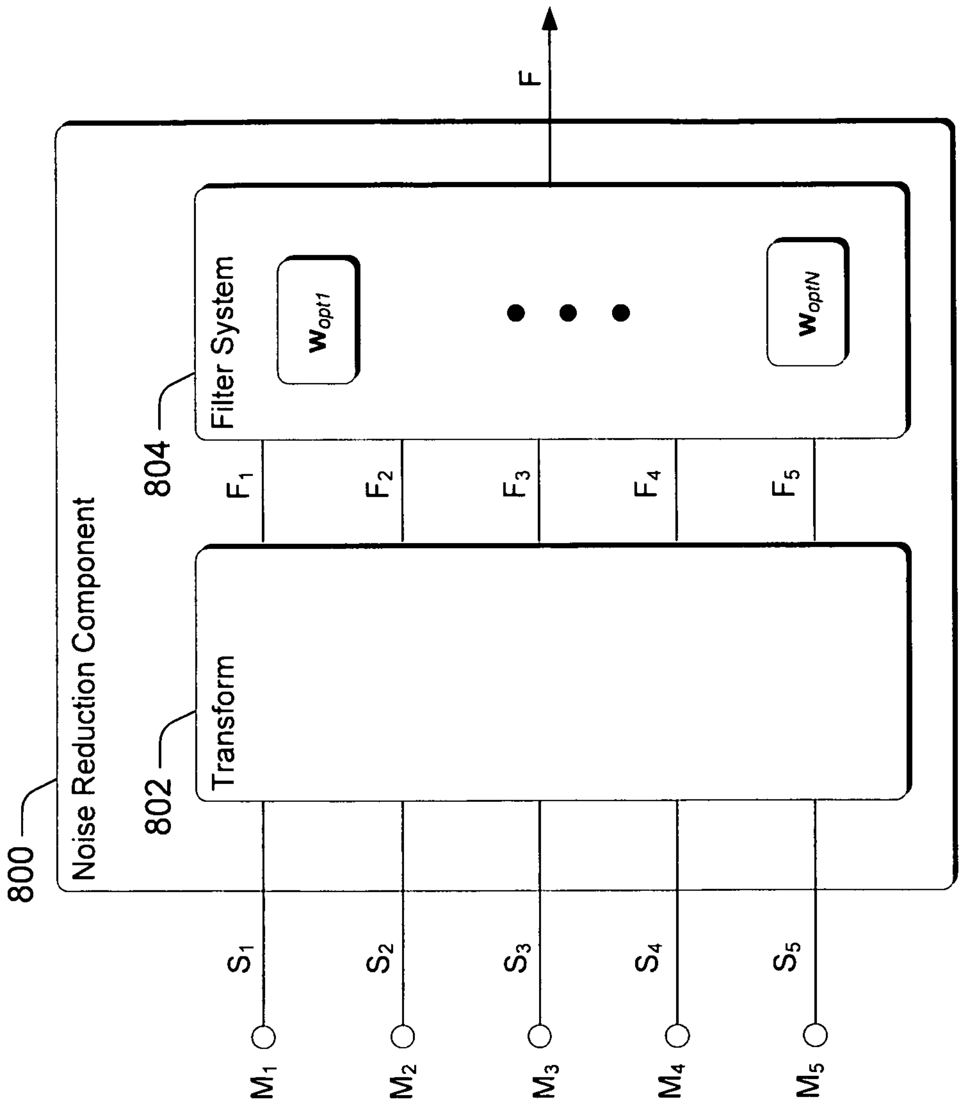
FIG. 8 illustrates a noise reduction component in accordance with one embodiment.

As an example, consider FIG. 8 which illustrates an exemplary noise reduction component 800. In the illustrated and described embodiment, noise reduction component 800 comprises a transform component 802 and a filter system 804.

In this example, each microphone (represented as $M_1$, $M_2$, $M_3$, $M_4$, and $M_5$) of the microphone array records sound samples over time in the time domain. Each of the corresponding sound samples is designated respectively as $S_1$, $S_2$, $S_3$, $S_4$, and $S_5$. These sound samples are then transformed by transform component 802 from the time domain to the frequency domain. Any suitable transform component can be used to transform the samples from the time domain to the frequency domain. For example, any suitable Fast Fourier Transform (FFT) can be used. In a preferred embodiment, a Modulated Complex Lapped Transform (MCLT) is used. FFTs and MCLT are commonly known and understood transforms.

The transform component 802 produces samples in the frequency domain for each of the microphones (represented as $F_1$, $F_2$, $F_3$, $F_4$, and $F_5$). These frequency samples are then passed to filter system 804, where the samples are filtered in accordance with the filters that were computed above. The output of the filter system is a frequency signal F that can be transmitted to other game players, or further processed in the accordance with the processing that is described below in the section entitled "Threshold Processing of the Filtered Output Signal." Filter system 804 automatically combines the several microphone signals into a single signal. In the described embodiment, this is done automatically since the filter is of the form:

$$Y(\omega,f)=\Sigma_n w(n,\omega)X(n,\omega,f),$$

Where X(n,ω,f) is the ω-th coefficient of the transform of the signal at the n-th microphone, for the f-th frame, and w(n,ω) is the corresponding filter coefficient, and where the summation is over n.

The frequency signal F is a signal that constitutes an estimated speech signal having a reduced noise component. This frequency domain filtered signal F can be passed on directly to a codec or other frequency domain based processing, or, if a time domain signal is desired, inverse transformed.

Threshold Processing of the Filtered Output Signal

Figure 9:
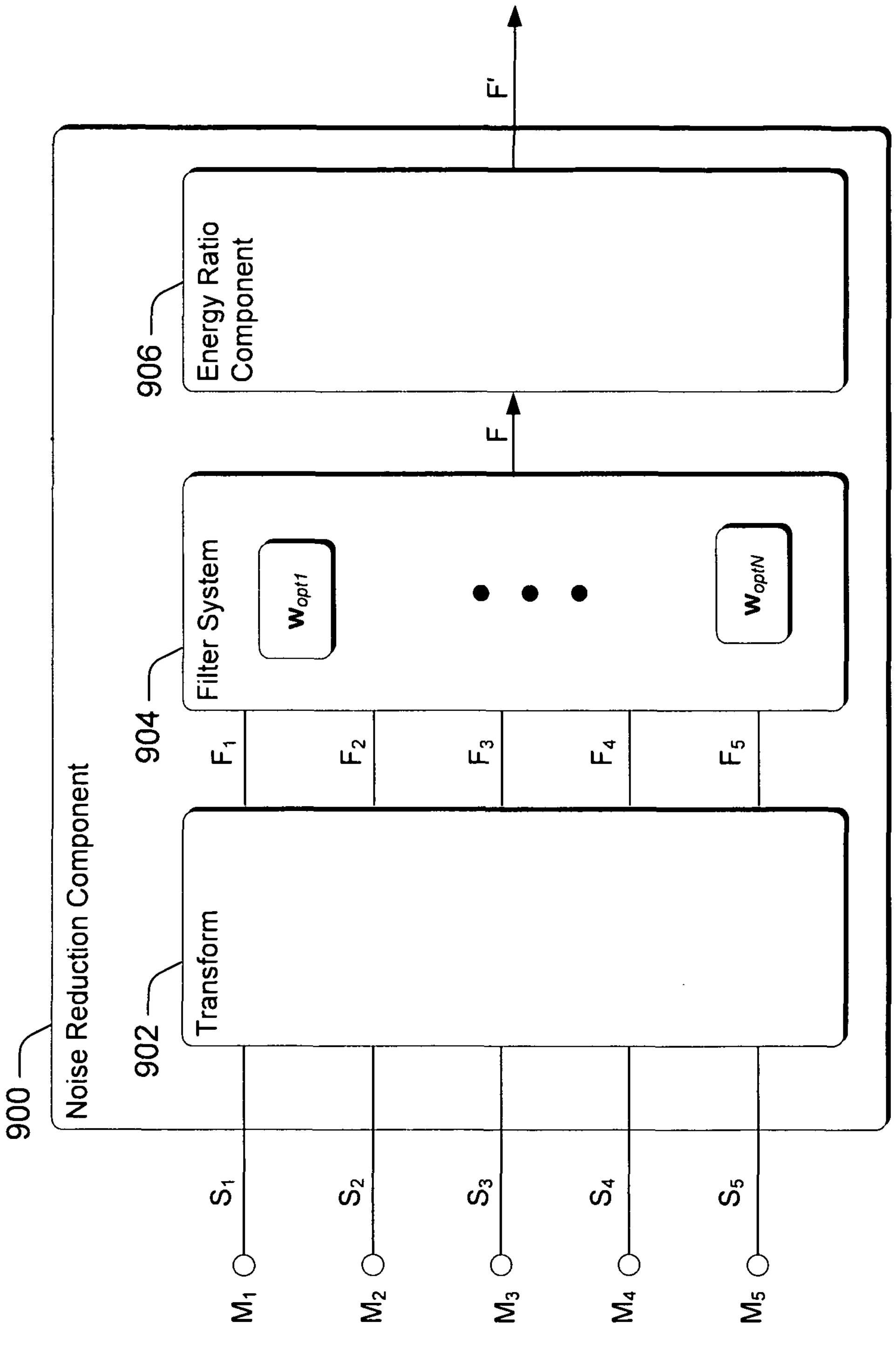
FIG. 9 illustrates a noise reduction component in accordance with one embodiment.

FIG. 9 shows a noise reduction component in accordance with one embodiment generally at 900. In this example, noise reduction component 900 comprises a transform 902 and a filter system 904 which, in this embodiment, are effectively the same as transform 802 and filter system 804 in FIG. 8. In this example, however, an energy ratio component 906 is provided and receives the filtered output signal F for further post processing.

Here, the energy ratio component is configured to further process a filtered output signal to further attempt to remove noise components to provide an even more noise-attenuated filtered signal. For an understanding of the principles upon which the energy ratio component is constructed, consider the following.

For purposes of the explanation that follows, we will assume that the processing that takes place utilizes a filtered output signal which is an aggregation of all of the signals captured by the microphone array. In the example of FIG. 9, this signal constitutes the signal F. The ratio is measured between (one or more of) the individual microphone signals, and the estimated speech. In other words, one possible implementation is:

$$R=E_{ch1}/E_f.$$

Other possible implementations include:

$$R=(\Sigma_n E_{chn})/N/E_f.$$

Figure 10:
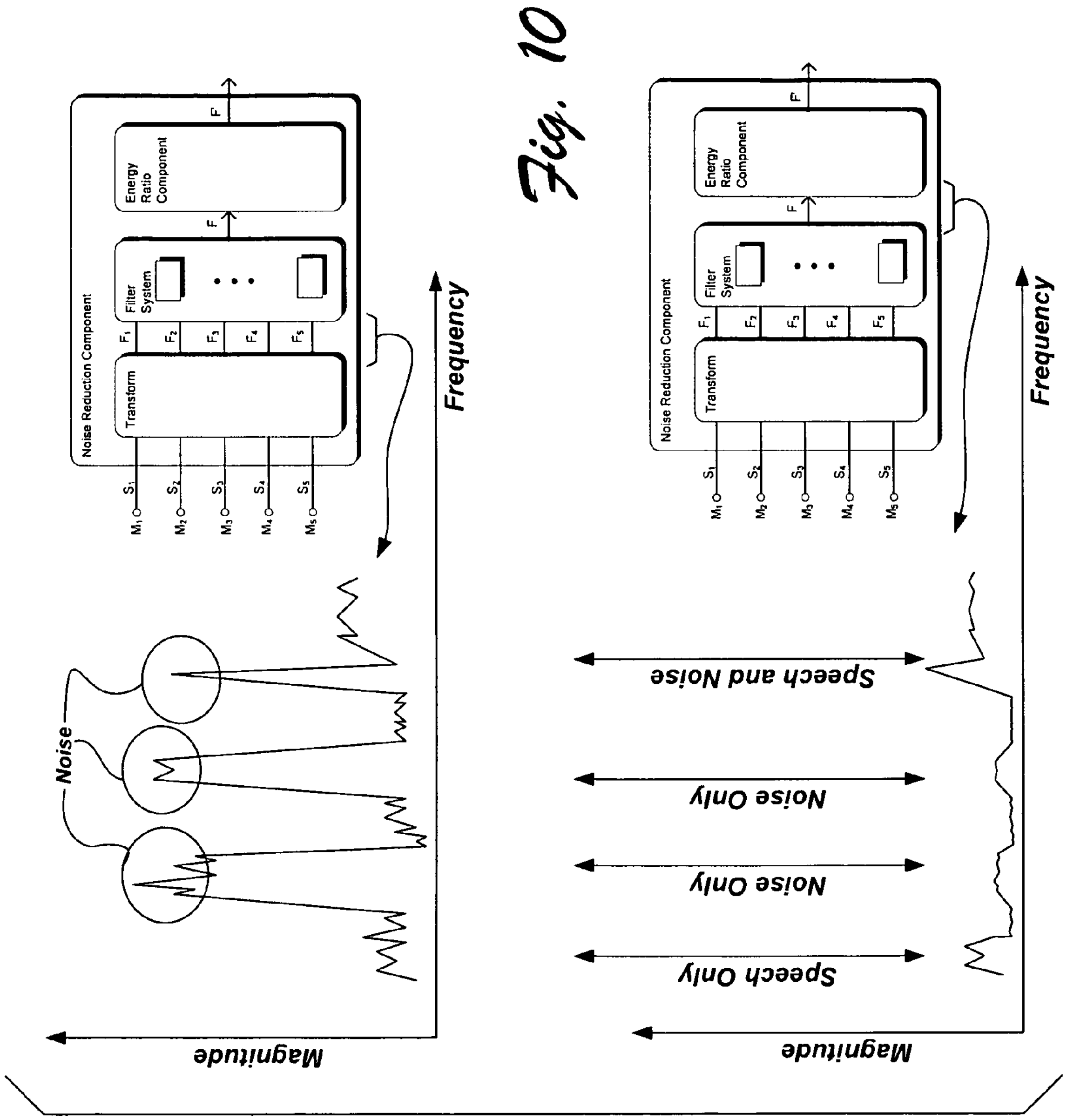
FIGS. 10 and 11 illustrate frequency/magnitude plots that are useful in understanding concepts underlying one embodiment.

Consider first FIG. 10 which illustrates two waveforms plotted in terms of their frequency and magnitude. The topmost plot comprises a transformed signal that contains speech only, noise only and speech and noise components. This transformed signal may correspond to one of the signals (or an average of a few of them) at the output of transform component 902 in FIG. 9. The bottommost plot comprises the filtered output signal that corresponds to the transformed signal of the topmost plot. That is, the bottommost plot corresponds to the signal at the output of filter system 904.

Now consider the differences between the signals of the topmost and bottommost plots. These differences are best appreciated in light of the speech only, noise only and speech and noise components of the signals. Notice first that the speech only component (which is labeled as such) has experienced little if any change as a result of undergoing filtering by filter system 904. That is, the magnitude or energy of the signal component corresponding to speech only has not meaningfully changed as a result of being filtered.

Now consider the noise only components of the signals. Notice first that the magnitude or energy of the transformed signal in the topmost plot is fairly large when compared with the magnitude or energy of the corresponding components in the bottommost plot. That is, the filter system has successfully filtered out most of the noise from the transformed signal leaving only a small noise component whose magnitude or energy is fairly small in relation to the transformed signal that was filtered.

Now consider the speech and noise component of the signal. This is the component that includes both noise and speech and would correspond, for example, to the situation where a game player is speaking while pressing buttons on the game controller. Notice here that the transformed signal component of the topmost plot has a magnitude or energy that is comparably as large as the noise only component. Yet, after filtering, the filtered signal component has a magnitude or energy that is somewhat lesser in magnitude and comparable to the speech only component. This is to be expected as the filter system has successfully filtered out some of the noise from the noise and speech signal, leaving only the speech component of the signal and perhaps a small amount of noise that was not removed.

From a mathematical standpoint, the differences between the transformed signal and the filtered signal can be appreciated as a ratio of the energy of the signal before filtering to the energy of the signal after filtering or $E_t/E_f$. For ease of illustration, consider that the energy of the noise only component before filtering has a magnitude of 10 and that after filtering it has a magnitude of 2. Further, consider that energy of the speech only component has a magnitude of 5 before filtering and a magnitude of 5 after filtering. Further, consider that the energy of the speech and noise component has an energy of 10 before filtering and an energy of 6 after filtering. These relationships are set forth in the table below.

| Signal Component | $E_t$ | $E_f$ | Ratio |
|---|---|---|---|
| Noise Only | 10 | 2 | 5 |
| Speech Only | 5 | 5 | 1 |
| Speech/Noise | 10 | 6 | 1.66 |

What the ratio indicates is that there is a range of magnitudes that indicates the noise only component of the filtered signal. For example, the noise only component of the signal above has a ratio of 5, while the speech only and speech and noise ratios are 1 and 1.66 respectively. With this relationship, the energy ratio component 906 (FIG. 9) can identify those portions of the filtered output signal that correspond to noise only, and can further attenuate the segments identified as noise. The energy ratio component can additionally identify those portions of the filtered output signal that correspond to speech only and speech and noise and can leave those portions of the signal untouched.

Figure 11:
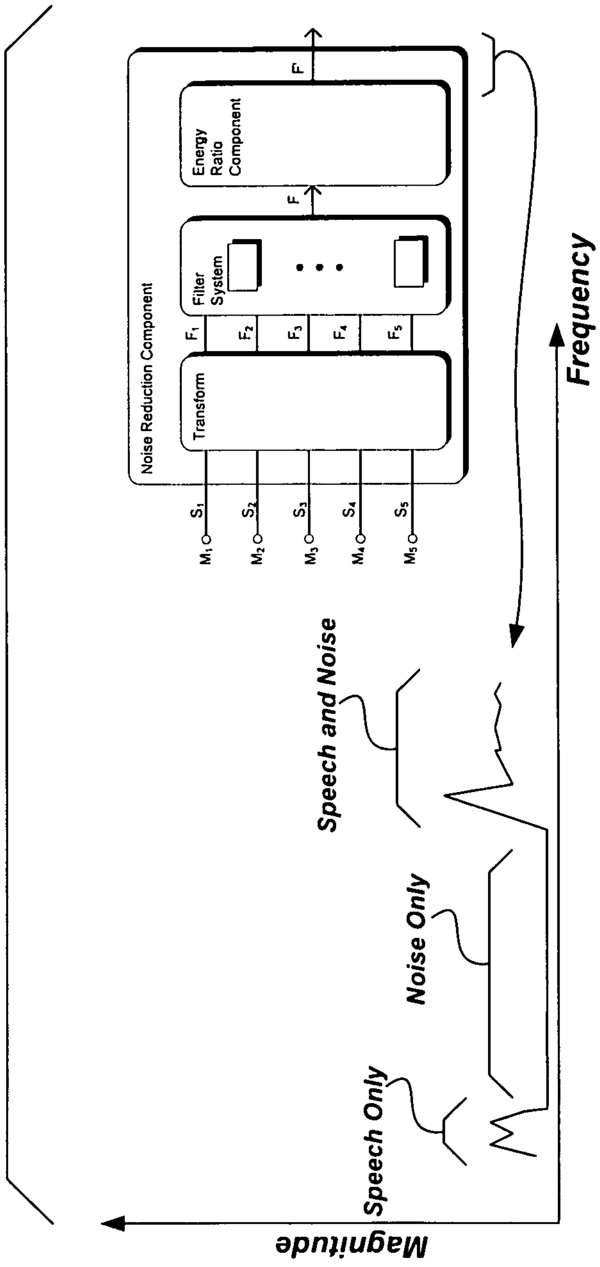

As an example, consider FIG. 11 which comprises the signal F' at the output of the energy ratio component. A comparison of this plot with the bottommost plot of FIG. 10 indicates that those portions of the filtered output signal that correspond to speech only and speech and noise have been left untouched. However, that portion of the filtered output signal that corresponds to the noise only component has been further filtered so that little if any of the original noise only component remains.

Figure 12:
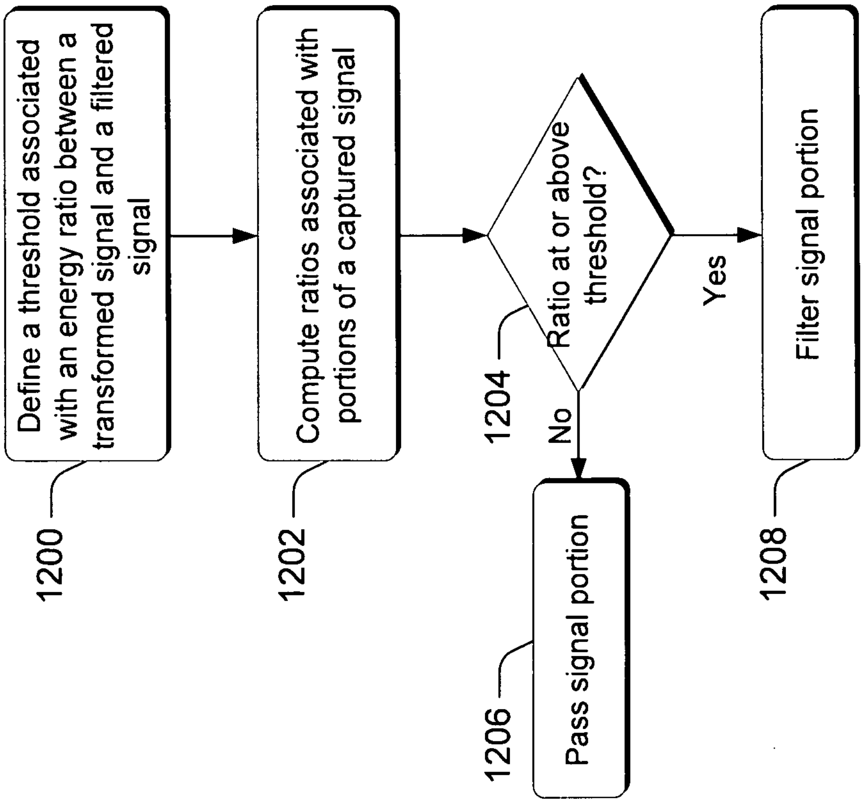
FIG. 12 is a flow diagram that describes steps in a method in accordance with one embodiment.

FIG. 12 is a flow diagram that describes steps in a method in accordance with one embodiment. The method can be implemented in any suitable hardware, software, firmware or combination thereof. In the illustrated and described embodiment, the method can be implemented in software that is hard-coded in a device such as a game console.

Step 1200 defines a threshold associated with an energy ratio between a transformed signal and a filtered signal. The threshold is set at a value above which, a signal portion is presumed to constitute noise only. An exemplary method of calculating a ratio is described above. Step 1202 computes ratios associated with portions of a captured signal. An example of how this can be done is given above. Step 1204 determines whether the computed ratio is at or above the threshold. If the computed ratio is not at or above the threshold, then step 1206 does nothing to the signal and simply passes the signal portion. If, on the other hand, the computed ratio is at or above the threshold (thus indicating noise only), step 1208 further filters to the signal portion to suppress the noise.

In the previous example, the additional noise attenuation was obtained by a thresholding mechanism. This hard threshold can be substituted by a gain that varies with the energy ratio. For example, a preferred embodiment sets this gain to:

$$G=0.5(1-\cos(pi*E_t/E_f))$$

A person skilled in the art will know that many other functions can be used with similar effect.

Associating Individual Filters with Individual Noise Sources

In the above-described embodiment, the efficiency of the spatial filter depends on how well the noise is represented by the $R_{nn}$ component, and how well the speech signals are represented by the $R_{ss}$ component. In the particular example described above, several of the types of noise are known in advance. With this knowledge of the noise types, the filter system was constructed and trained to generally recognize noise and speech and filter the signals across the microphone array accordingly.

Now consider the following. From the perspective of knowing the noise types in advance, one also knows some of the particular sources of the noise types. For example, one noise type is a button click. This noise type can have several sources, i.e. the individual buttons that are present on the game controller. Each individual button may, however, have a noise profile that is different from other buttons. Thus, while in general, the buttons collectively constitute a source of the noise type, each individual button can and often does contribute its own unique noise to the mix. By recognizing that individual user input mechanisms, such as buttons, can have their own unique noise profile, individual filters or filter systems can be built for each of the particular noise sources. In operation then, when the system detects that a particular source of the noise has been engaged by the user or player, the system can automatically select the appropriate associated filter and use that filter to process the corresponding portion of the signal that is captured.

Figure 13:
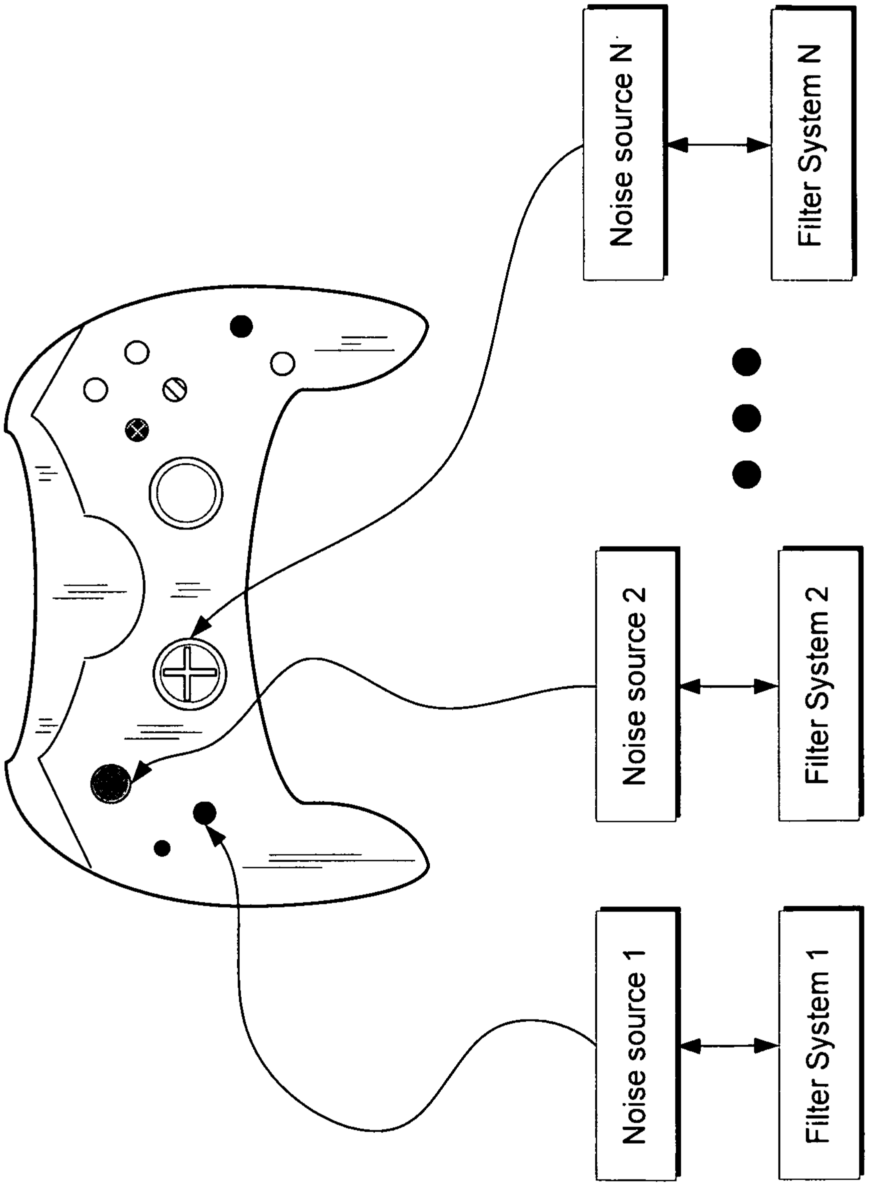
FIG. 13 illustrates a game controller and associated filter systems in accordance with one embodiment.

As an example, consider FIG. 13. There, a collection of filter systems is shown, each being associated with a particular noise source. For example, filter system 1 is associated with noise source 1 which might comprise the indicated button. Similarly, filter system 2 is associated with a particular noise source that might comprise the indicated button; likewise, filter system N is associated with a particular noise source that might comprise the indicated button.

By having individual filter systems associated with individual noise sources, when the particular noise source is engaged by the user or player, the appropriate filter system can be selected and used. For example, game controllers all include a signal-producing mechanism that produces a signal when the user depresses a particular button. This produced signal is then transmitted to the game console which uses the signal to affect, in some manner, the game that the player is playing. In the present case, this signal can further be used to indicate that the player has depressed a particular button and that, as a result, the appropriate filter should be selected and used.

Even if the information about the noise source is not readily available, it can still be detected using, for example, a classification procedure, which can be performed in many ways that are well known to someone skilled in the art. Examples of such classification schemes may include neural network classifiers, support vector machines and other.

Figure 14:
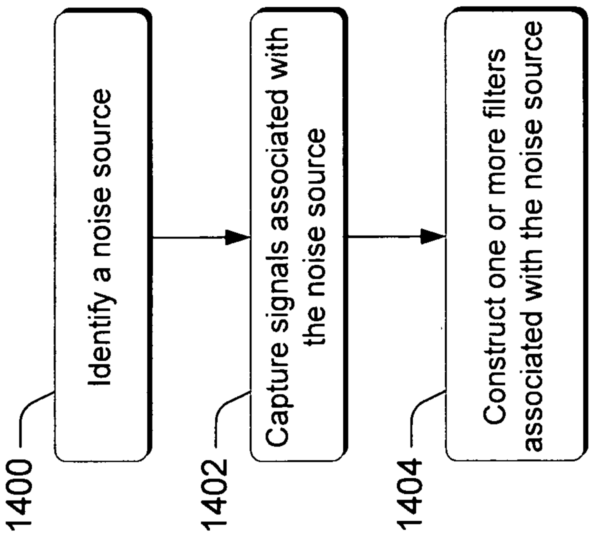
FIG. 14 is a flow diagram that describes steps in a method in accordance with one embodiment.

FIG. 14 is a flow diagram that describes steps in a training method in accordance with one embodiment. Step 1400 identifies a noise source. In the above example, noise sources are associated with individual user input mechanisms that reside on a game controller. Step 1402 captures signals associated with the noise source. This step can be accomplished in a manner that is similar to that described above with respect to step 502 in FIG. 5. Step 1404 constructs one or more filters associated with the particular noise source. Filter construction can take place in a manner that is similar to that described above with respect to step 506 in FIG. 5. Accordingly, FIG. 14 describes a method that can be considered as a training method in which individual filters are designed to recognize individual sources of noise.

Figure 15:
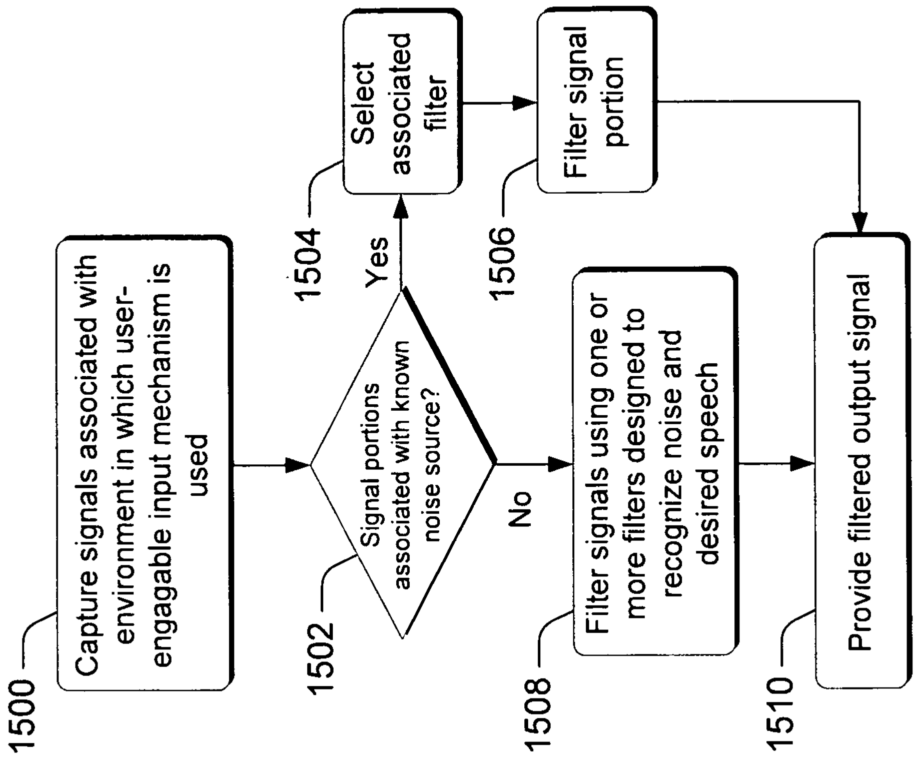
FIG. 15 is a flow diagram that describes steps in a method in accordance with one embodiment.

FIG. 15 is a flow diagram that describes steps in a noise-reduction method in accordance with one embodiment. Step 1500 captures signals associated with an environment in which a user-engagable input mechanism is used. This step can be implemented in a manner that is similar to that described above with respect to step 600 in FIG. 6. Step 1502 determines whether a signal portion is associated with a known noise source. As noted above, this step can be implemented by detecting when a particular button is depressed by a user or player. If a signal portion is associated with a known noise source, then step 1504 selects the associated filter and step 1506 filters the signal portion using the selected filter to provide a filtered output signal (step 1510). If, on the other hand, step 1502 is not able to ascertain whether a portion of the signal corresponds to a particular known noise source, step 1508 filters the signal using one or more filters designed to recognize noise and desired speech. This step can be implemented using a filter system such as the one described above. Accordingly, this step produces a filtered output signal.

Conclusion

The various embodiments described above provide methods and systems that can meaningfully reduce noise in a signal and isolate speech components associated with the environments in which the methods and systems are employed.

Although the invention has been described in language specific to structural features and/or methodological steps, it is to be understood that the invention defined in the appended claims is not necessarily limited to the specific features or steps described. Rather, the specific features and steps are disclosed as preferred forms of implementing the claimed invention.

The invention claimed is:

1. A method comprising:

providing a computing device having an array of microphones comprising one or more microphones; and using the microphone array, training the computing device to recognize noise that emanates from a location on the computing device, the training including at least a noise-capturing training phase in which a user produces button clicking noise by physically manipulating at least two buttons on the computing device and the button clicking noise is captured, the training enabling the computing device to create a different noise profile for each of the at least two buttons.

2. The method of claim 1, wherein the computing device comprises a keyboard.

3. The method of claim 1, wherein the computing device comprises a game controller.

4. The method of claim 1, wherein the computing device comprises a laptop computer.

5. The method of claim 1, wherein training the computing device further comprises training the computing device to recognize speech that emanates from a location outside of the computing device.

6. A system comprising:

a housing;

at least a first user input mechanism and a second user input mechanism supported by the housing;

a processor;

a computer-readable media;

a microphone array comprising one or more microphones;

a noise reduction component comprising at least a first filter system and a second filter system embodied on the computer-readable media, the first filter system configured to recognize noise made from manipulation of the first user input mechanism, and the second filter system configured to recognize noise made from manipulation of the second user input mechanism; and the noise reduction component configured to cause the processor to use the first filter system and the second filter system to filter noise from speech captured by the microphone array.

7. The system of claim 6, further comprising a third filter system configured to recognize noise from one or more known sources that are fixed relative to the microphone array.

8. The system of claim 6, further comprising a third filter system configured to recognize noise from one or more known sources that are located on the housing.

9. The system of claim 7, wherein at least one of the one or more known sources are not located on the housing.

10. The system of claim 7, wherein at least one of the one or more known sources are located on the housing, and at least one other of the one or more known sources are not located on the housing.

11. A game controller comprising:

an array of microphones comprising one or more microphones; and a trained filter system comprising at least a speech filter system and a noise filter system, the speech filter system configured to recognize speech signals that emanate from a fixed location relative to the microphone array, and the noise filter system configured to recognize noise that emanates from at least a first button on the game controller and a second button on the game controller, the fixed location relative to the microphone array located outside of the game controller, the filter system configured to be trained using at least a noise capturing training phase that captures noise that emanates from manipulation of the first button and the second button on the game controller, the noise capturing training phase enabling the filter system to create a first noise profile for the first button and second noise profile for the second button, and the filter system configured to filter noise from speech captured by the array of microphones.

12. The game controller of claim 11, wherein the trained filter system is further configured to recognize noise that emanates from other locations that are fixed relative to the microphone array.

13. The game controller of claim 11, wherein the trained filter system is further configured to recognize noise that emanates from other locations that are located on the game controller itself.

14. The game controller of claim 11, wherein the trained filter system is further configured to recognize noise that emanates from other locations that are not located on the game controller itself.

15. The game controller of claim 12, wherein:

at least some of the other locations are located on the game controller itself; and at least some of the other locations are not located on the game controller itself.

16. The game controller of claim 11, wherein the filter system is configured to filter undesired speech that emanates from particular locations relative to the game controller.

* * * * *